United States Patent
Kayani

[19]

[11] Patent Number: 5,922,959
[45] Date of Patent: Jul. 13, 1999

[54] METHODS OF MEASURING CURRENCY LIMPNESS

[75] Inventor: Sohail Kayani, Irving, Tex.

[73] Assignee: Currency Systems International, Dallas, Tex.

[21] Appl. No.: 08/730,711

[22] Filed: Oct. 15, 1996

[51] Int. Cl.$^6$ .................................................. G01N 29/04
[52] U.S. Cl. .............................. 73/597; 73/599; 73/627; 73/159; 209/534; 209/590
[58] Field of Search .......................... 73/159, 597, 598, 73/599, 600, 602, 620, 624, 625, 627, 628, 629; 209/534, 576, 577, 587, 588, 590, 599, 699; 364/551.01

[56] References Cited

U.S. PATENT DOCUMENTS

| | | | |
|---|---|---|---|
| 4,365,508 | 12/1982 | Loftus | 73/159 |
| 4,446,735 | 5/1984 | Weilacher | 73/597 |
| 4,463,607 | 8/1984 | Hilton | 73/587 |
| 4,465,192 | 8/1984 | Ohba . | |
| 4,519,249 | 5/1985 | Hunt | 73/596 |
| 4,548,081 | 10/1985 | Wolthausen | 73/584 |
| 4,677,682 | 6/1987 | Miyagawa . | |
| 4,845,917 | 7/1989 | Omura . | |
| 4,905,840 | 3/1990 | Yuge . | |
| 5,012,932 | 5/1991 | Omura . | |
| 5,105,364 | 4/1992 | Kawamura . | |
| 5,182,722 | 1/1993 | Hain | 364/551.01 |
| 5,201,424 | 4/1993 | Hain | 209/534 |

*Primary Examiner*—Hezron Williams
*Assistant Examiner*—Rose M. Miller
*Attorney, Agent, or Firm*—Carstens, Yee & Cahoon; Colin P. Cahoon

[57] ABSTRACT

Measuring the limpness of a note is necessary to separate a worn note out of circulation. Several methods are disclosed which can be used either alone or in combination to test for limpness. One method measures the note's ability to reflect light or transmit the light. Another method measures the response of the note to an acoustic wave. Another method measures the note's deflection to a pressure or force. Yet another method measures the dielectric value of the note when placed between the plates of a capacitor. A final method involves measuring the thermal conductivity of the note. In each case, a limp note will produce distinguishable results from a stiff note.

8 Claims, 2 Drawing Sheets

METHODS OF MEASURING CURRENCY LIMPNESS

TECHNICAL FIELD OF THE INVENTION

The present invention relates to methods of measuring the limpness of currency. Specifically, the currency, in the form of paper notes, is subjected to a test or a series of tests to determine if it has worn beyond an acceptable level of limpness.

BACKGROUND OF THE INVENTION

Automated, high-volume currency processing is a growing international industry affecting numerous aspects of the distribution, collection, and accounting of paper currency. Currency processing machines can be designed to detect numerous features of currency notes that pass several detectors on a conveyor in order to sort the currency and identify counterfeit or reject notes. For example, prior art currency processing machines are capable of detecting various physical characteristics of notes such as soiling level, optical quality, rips and tears, and can quantify missing portions of the notes. Data collected by detecting one or more of these physical characteristics can be compared to a set fitness standard when determining if an individual note should be rejected, and thereby taken out of circulation, or sorted for future distribution.

Currency notes are typically embedded with fibers, for example cotton fibers and wood pulp, giving the note a certain level of rigidity or stiffness. As the note is placed in circulation and manipulated while in use, the fibers gradually break down and the note loses its rigidity, or, conversely, the limpness of the note increases with use. Limp notes pose a number of problems in commerce. For example, limp notes can jam or tear in automatic currency handling devices. Likewise, torn currency poses a problem for merchants who do not want to risk accepting currency that is not negotiable. It may be more difficult to detect counterfeit notes from authentic currency if the notes are badly worn and limp. Therefore, a need exists for a method of testing currency for limpness. By developing a method for determining the limpness of a single note, a currency processing machine could be used to incorporate this method with other tests for physical characteristics of a note to more accurately determine if a note should be pulled from circulation. The single parameter of a note limpness could also provide a standard for rejecting a note. With this new detection method of quantifying the limpness of a note, currency distributors would also have a tool for monitoring the average lifespan of notes in circulation by comparing limpness measurements with the date of initial circulation of notes processed.

The present invention provides various methods for determining the limpness of a note and, thereby, addressing the many needs for determining this physical characteristic.

SUMMARY OF INVENTION

Several methods have been developed to measure the relative limpness of a note. There is no absolute value for limpness above which an issuing authority will pull a note from circulation. Instead, a value can be determined which is relative to a new note or some other standard. The methods measure any combination of factors including the light reflectivity of the note or the transmissivity of the note to light. Its ability to reflect or transmit acoustic waves can be measured. Further, its ability to resist deflection can be used as a measure of limpness. The dielectric value of the note can also be measured by placing the note between the flat plates of a capacitor. Finally, the note's thermal hysteresis can be measured. In each of these methods, the performance of a worn, limp note differs from the performance of a new, stiff note.

These methods can be used alone or in combination. Further, any single test can be applied several times to different areas of the same note. By accumulating more than a single test result, the likelihood of separating an acceptable note or passing a limp note will be reduced.

BRIEF DESCRIPTION OF THE DRAWINGS

Further objects and advantages of the present invention will become apparent from the following detailed description when read in conjunction with the accompanying drawings, in which.

DETAILED DESCRIPTION OF PREFERRED EMBODIMENT

The present invention relates to methods of determining the limpness of currency. The currency of many nations is commonly printed on special papers which are resilient and difficult to duplicate. The paper currency, when initially printed, is very stiff. This stiffness is the result of long fibers embedded in the paper. For example, many currencies use papers with cotton fiber content. These cotton fibers provide much of the strength and stiffness to the note. However, during use, the note will be folded and crumpled and otherwise handled roughly. This rough handling will over time break down the embedded fiber, resulting in a note that is noticeably limper than new currency.

Figure 1A:
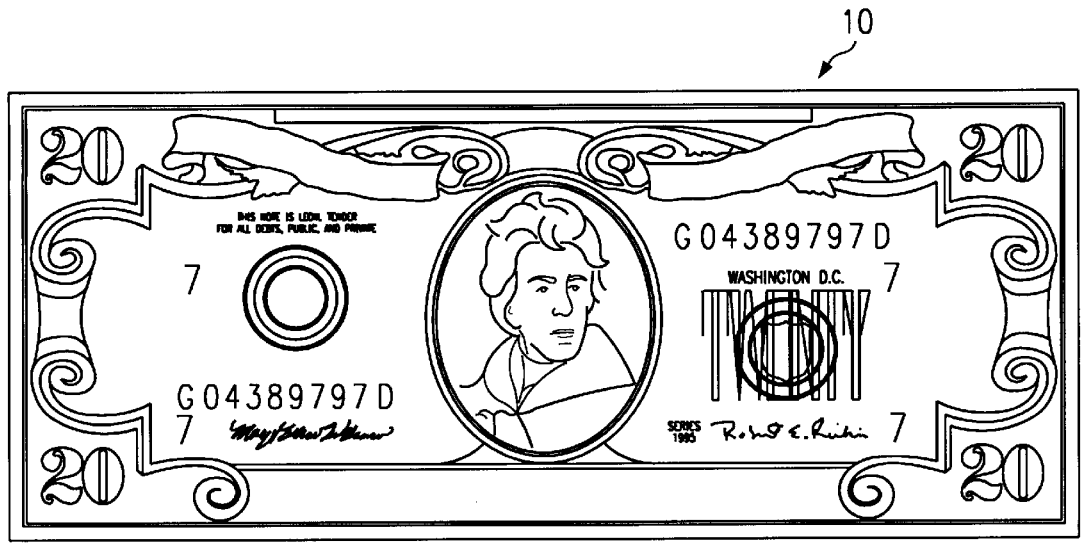
FIGS. 1a and 1b illustrate a new and stiff note of currency and a limp or worn note, respectively.
Figure 1B:
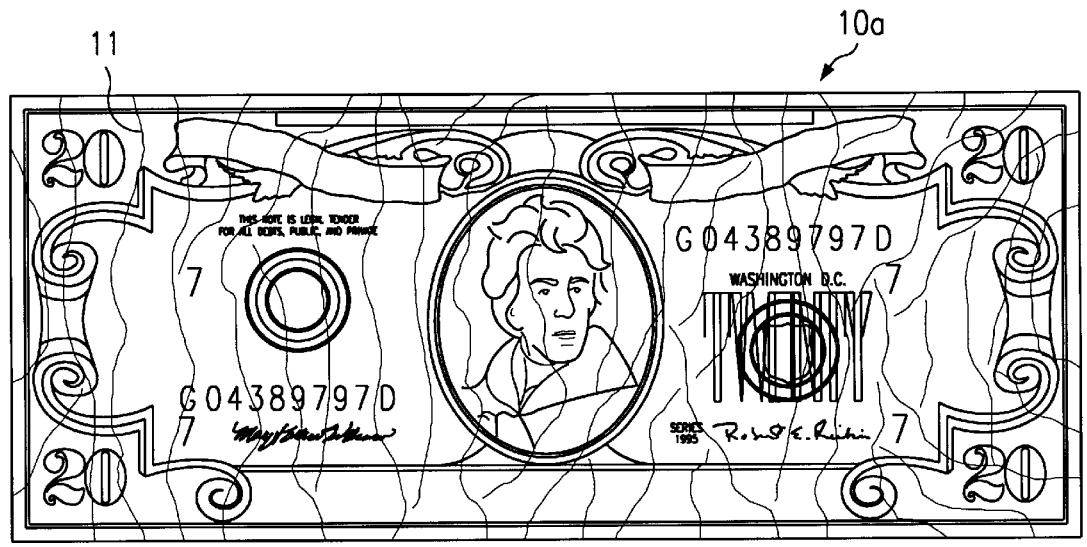

FIG. 1a illustrates a new, stiff note 10. The note contains fibers which are mixed throughout the thickness of the note. The fibers are not necessarily oriented in any particular direction. But, the sum of their individual stiffness results in the overall stiffness of the note. FIG. 1b illustrates a similar note 10a which has been used in circulation. Over time the note will develop crinkles 11 along which embedded fibers have become weakened or broken. Eventually, the entire note may become soft and limp as numerous embedded fibers are worn down and broken. The limpness of the note makes it less suitable for use in commerce. It is more likely to tear or jam in automatic currency handling devices. Limp notes are also more susceptible to tearing in ordinary use and are generally less durable than stiff notes. Thus, it is desirable to remove limp notes from circulation.

Figure 2:
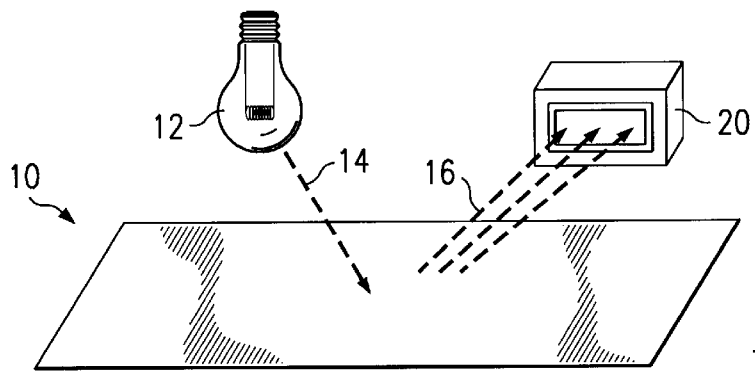
FIG. 2 illustrates the limpness test utilizing either the reflectivity or transmissivity of the worn note.

FIG. 2 illustrates the use of a light source 12 to measure the limpness of a note 10. The light source 12 emits a light beam 14. The beam can be coherent. A portion 16 of the light 14 will be reflected off of the surface of the note, while a portion 18 will pass through the note. A detector 20, or an array of detectors, can be placed near the note to measure the reflected light 16, while another detector 22 can be used to measure the transmitted light 18. Various light sources can be used. If reflected light is to be the measure, an ultraviolet light source is preferred. If transmitted light is the measure, then an infrared source is preferred. Suitable detectors must be used to detect the reflected or transmitted light. A photomultiplier or a silicon photo diode can also be used to amplify the signal produced by the reflected or transmitted light. A limper note will tend to scatter more light than a crisp note, thus producing a lower relative signal from the reflected light detector 20 or a broader reflective pattern across an array of detectors. Conversely, a limper note will allow more infrared light to pass, resulting in a higher relative output signal from the infrared detector 22.

Figure 3:
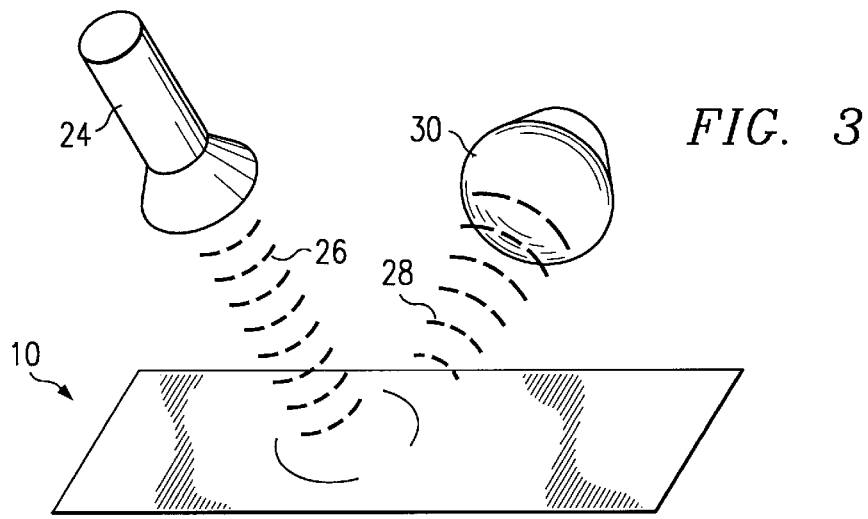
FIG. 3 illustrates the use of an acoustic source and detector to measure the limpness of a note.

FIG. 3 illustrates a method of measuring limpness by testing the response of the note 10 to an acoustic source 24. The acoustic source 24 will produce an acoustic output wave 26 which will impact the surface of the note 10. The wave will be partly absorbed, and also partly reflected. The reflected portion 28 can be detected by a detector 30. The limper a note, the more energy it will absorb from the acoustic wave 26. This results in a lower relative output from the acoustic detector 30. A suitable acoustic wave source would be a piezoelectric transmitter receiver pair.

Figure 4:
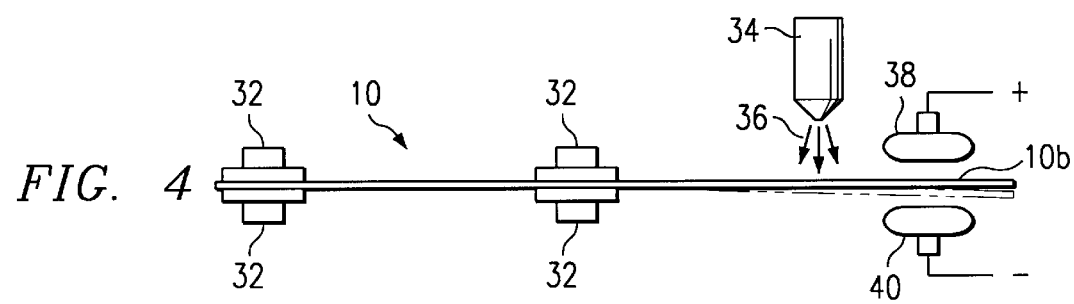
FIG. 4 illustrates the use of air pressure to deflect a portion of a note to determine the limpness of the note.

A limper note 10 also will display a lowered resistance to deflection. A test for limpness can therefore involve the application of a pressure to the note and a measurement of its deflection. FIG. 4 illustrates such a method. The note 10 can be sustained in a series of clamps 32 in such a way that a portion 10b of the note is cantilevered. An air pressure source 34 positioned near this cantilevered portion 10b of the note can apply a burst of air pressure 36. The pressure will tend to deflect the note. A limp note will deflect further than a stiff note. Sensing the amount of deflection can be accomplished any number of ways. For example, optical sensors can be positioned so that the deflected notes will block a beam directed at a sensor if the note is deflected more than a predetermined distance. Another method of sensing the deflections involves using the cantilevered portion 10b of the note as the dielectric between the plates 38, 40 of a capacitor. The movement of the note will change the overall value of the capacitor. Thus, a measurement of the capacitor's value will provide an indication of the movement, and hence limpness, of the note.

Figure 5:
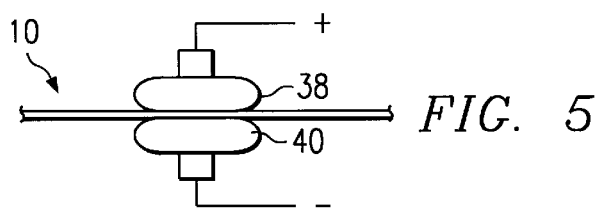
FIG. 5 illustrates the use of the dielectric value of the note stock to determine the limpness of the note; and, FIG. 6 illustrates a method of heating a note and measuring its heat capacity to determine limpness.

In a related method of detection of limpness, an undisturbed note 10 is simply used as the dielectric in a capacitor and placed between the plates 38, 40 of a capacitor, as shown in FIG. 5. The capacitor value varies according to the number of broken fibers in the detected area of the note. Therefore, a relative capacitor valve can be correlated to the limpness of the note.

Figure 6:
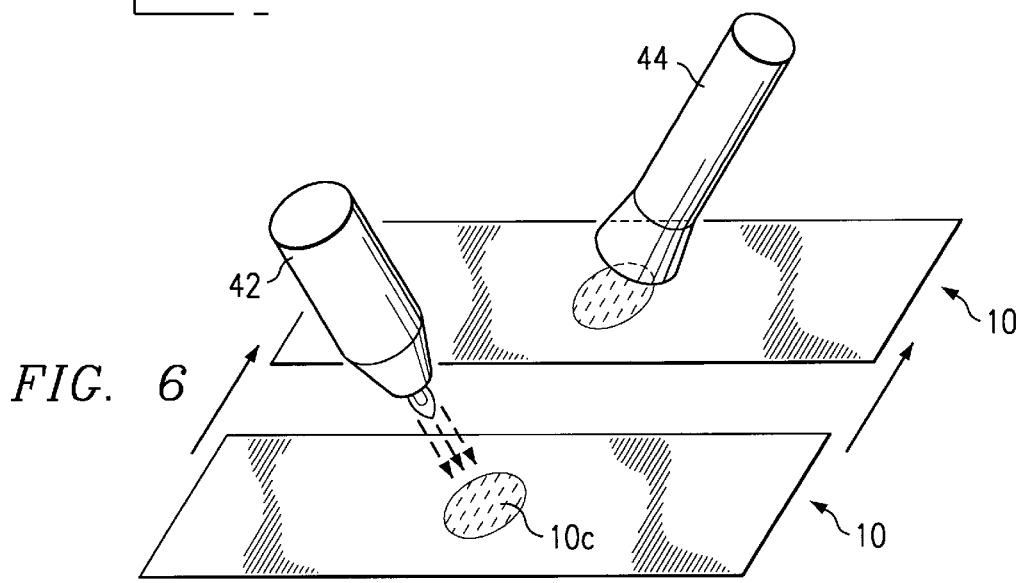

Another method involves a measurement of the heat capacity of the note. In other words, the note's ability to dissipate heat is a function of the notes limpness and wear. In this method, as shown in FIG. 6, a portion 10c of the note 10 is heated by a thermal source 42 to a first temperature. At a predetermined time, the temperature of that same portion is measured by a thermal detector 44. The difference in temperature can be translated into a thermal conductivity or hysteresis coefficient for the note. This coefficient is related to the limpness of the note.

A currency processing apparatus for measuring the limpness of notes would necessarily transport the notes from a first location to a second location while performing the tests and separating the limp notes from the stiff notes. For the thermal conductivity test discussed above, the note might be heated at the beginning of the process and measured at a second location to allow time for cooling. However, a test for light reflectivity would be measured almost simultaneously with the application of the test light. The currency processing apparatus would have a transport mechanism, which takes the note between various test locations. The apparatus could utilize any single one of the above mentioned tests by itself or in combination with any of the other tests. For example, the deflection test could be coupled with the acoustic response test. A combination of tests could produce a more complete separation of limp notes. Further, any one of these test could be performed on more than one test area on the note. This would take into account variations across the surface of the note. For example, the light reflectivity or transmissivity test could be performed on two or three locations on any single note.

Although preferred embodiments of the present invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of parts and elements as fall within the scope of the appended claims.

I claim:

1. A method of measuring the limpness of a note comprising the steps of:

(a) emitting an acoustic wave so that the wave is incident on the note;

(b) measuring a portion of the acoustic wave off the note; and, (c) correlating the difference between the emitted acoustic wave and the measured acoustic wave reflected off the note to a limpness value.

2. A method of measuring the limpness of a note comprising the steps of:

(a) emitting an acoustic wave so that the wave is incident on the note;

(b) measuring a portion of the acoustic wave reflected off the note; and, (c) determining the limpness of the note from the measured portion of the acoustic wave at one or more locations on the note.

3. A method of measuring the limpness of a note comprising the steps of:

(a) emitting an acoustic wave so that the wave is incident on the note:

(b) measuring a portion of the acoustic wave reflected off the note; and, (c) determining the limpness of the note from the measured portion of the acoustic wave along with a second method for determining currency limpness to determine a limpness value.

4. The method of claim 3 wherein the second method for determining currency limpness comprises the steps of:

(a) emitting a light so it is incident on the note;

(b) measuring an amount of the light reflected off of the note; and, (c) determining the limpness of the note from the measured portion of the light.

5. The method of claim 3 wherein the second method for determining currency limpness comprises the steps of:

(a) emitting a light so it is incident on the note;

(b) measuring an amount of the light transmitted through the note; and, (c) determining the limpness of the note from the measured portion of the light.

6. The method of claim 3 wherein the second method for determining currency limpness comprises the steps of:

(a) capturing a first portion of the note;

(b) deflecting a second portion of the note with a pressure;

(c) measuring the deflection; and, (d) determining the limpness of the note from the measured deflection.

7. The method of claim 3 wherein the second method for determining currency limpness comprises the steps of:

(a) capturing a note between a capacitor's plates;

(b) measuring a capacitance across the capacitor plates; and, (c) determining the limpness of the note from the measured capacitance.

8. The method of claim 3 wherein the second method for determining currency limpness comprises the steps of:

(a) heating a portion of the note to a predetermined temperature;

(b) measuring the temperature for that portion after a predetermined time; and, (c) determining the limpness of the note from the measured temperature.

* * * * *